United States Patent [19]

Dufour

[11] 4,071,517
[45] Jan. 31, 1978

[54] SOLUBLE SALTS CONTAINING SULPHUR

[76] Inventor: Claude Dufour, 4, Rond-Point Saint-James, 92200 Neuilly, France

[21] Appl. No.: 611,988

[22] Filed: Sept. 10, 1975

[30] Foreign Application Priority Data

Sept. 10, 1974 France .................................. 74 30693

[51] Int. Cl.² .......................................... C07D 473/08
[52] U.S. Cl. ..................... 260/253; 424/253
[58] Field of Search ......................... 260/253; 424/253

[56] References Cited

U.S. PATENT DOCUMENTS

| 2,017,279 | 10/1935 | Grüter | 424/253 |
| 2,595,853 | 5/1952 | Horclois | 260/253 |
| 2,715,624 | 8/1955 | Szabo et al. | 260/253 |
| 3,562,273 | 2/1971 | Salat et al. | 260/253 |

Primary Examiner—Paul M. Coughlan, Jr.
Attorney, Agent, or Firm—Craig & Antonelli

[57] ABSTRACT

A double salt comprising a material obtained by heating a mixture of equi-molar proportions of a theophylline alkanoic acid having the formula:

$$R_1 - (CH_2)_n - COOH$$

wherein $R_1$ is a theophyllyl group which may be substituted by a halogen atom and $n$ is an integer from 1—4; an aminocarboxylic acid containing sulphur having the formula:

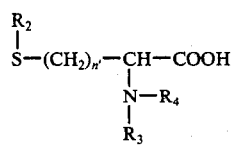

wherein $R_2$ represents a hydrogen atom, a methyl group, or a —$CH_2COOH$ group; $n'$ is an integer equal to 1 or 2; $R_3$ represents a hydrogen atom or a —$COCH_3$ group; $R_4$ represents a hydrogen atom and when sulphur and nitrogen are in a heteromonocyclic ring, $n'$ is 1, and $R_2$ and $R_4$ represent a methylene group and ethylene-diamine. The compounds have remarkable effects in the treatment of respiratory complaints.

15 Claims, No Drawings

SOLUBLE SALTS CONTAINING SULPHUR

This invention relates to new salts obtained by reacting (a) a theophylline alkanoic acid, which may be substituted by halogen in the theophyllyl group, on the one hand, and (b) an amino acid containing sulphur on the other, with (c) ethylenediamine. The new derivatives possess the structure of double salts which correspond to the general formula:

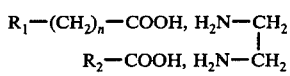

or with the ionic form:

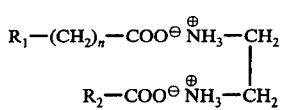

in which $R_1$ represents a theophyllyl group, which may be substituted by a halogen atom, $n$ is an integer of from 1 to 4, and $R_2$—COOH represents an aminocarboxylic acid containing sulphur. The amino acid contains 2 to 6 carbon atoms which may form a heterocycle, and can be N-acylated. The salts obtained according to the invention are well defined compounds which are soluble in water and are stable and practically neutral in aqueous solution. The invention relates more particularly to salts to which the following are the theophylline alkanoic acid $R_1$ — $(CH_2)_n$ — COOH:

7-theophylline acetic acid ($n = 1$) viz.

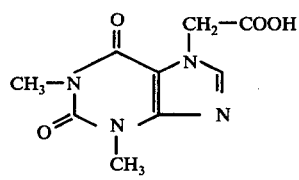

7-theophylline propionic acid ($n = 2$) viz.

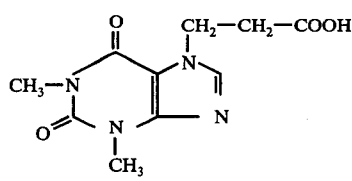

and 7-theophylline butyric acid ($n = 3$) viz.

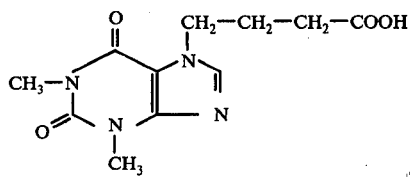

as well as the same acids when substituted in the 8-position by an atom of chlorine or bromine. The aminocarboxylic acid containing sulphur may be an α-aminoalkanoic acid containing sulphur in the molecule such as cysteine:

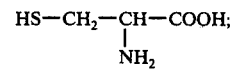

methionine:

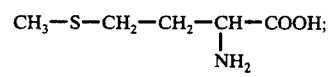

N-acetyl methionine:

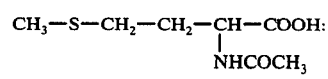

N-acetylcysteine;

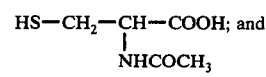

S-carboxymethylcysteine:

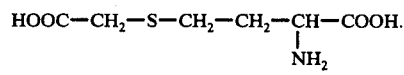

The aminocarboxylic acid containing sulphur may also be an acid having sulphur and nitrogen in a heteromonocyclic ring such as N-acetylthiazolidine carboxylic acid

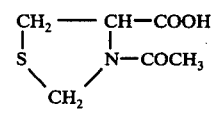

The salts having the above general formula having therapeutic applications, in particular, for treating complaints of the respiratory tract.

It will be appreciated from the above description of the aminocarboxylic acid containing sulphur that this acid may be represented by the following formula:

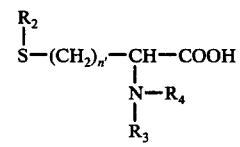

wherein $R_2$ represents a hydrogen atom, a methyl group or a —$CH_2COOH$ group; $n'$ is an integer equal to 1 or 2; $R_3$ represents a hydrogen atom or a —$COCH_3$ group; $R_4$ represents a hydrogen atom and when sulphur and nitrogen are in a heteromonocyclic ring, $n'$ is 1, and $R_2$ and $R_4$ represent a methylene group.

It is simple to prepare the products according to the invention by reacting, in a suitable solvent, equimolar quantities of a theophylline or halotheophylline alkanoic acid having the general formula $R_1(CH_2)_n$ COOH and of the amino acid containing sulphur with a molecular equivalent of ethylenediamine. The solvent used may either be water, or a mixture of water and an organic solvent such as ethanol, or a non-aqueous organic solvent such as dioxane or glycol. By concentrating the solvent in conventional manner, the desired salt crystallizes and is isolated using the conventional techniques or organic chemistry, e.g. by Centrifugation and vacuum drying.

To illustrate the preparation of the products according to the invention, a number of examples are given below. It is however emphasized that the exact particulars given relate to details of procedure, and that the relative proportions of reagents are not of a limiting nature.

1. The double salt of 1 mole of 7-theophylline acetic acid and 1 mole of methionine with 1 mole of ethylenediamine.

To a solution of 6.77 g (0.112 mole) of ethylenediamine and 16.7 g (0.112 mole) of methionine in 100 ml of water is added, while stirring, 26.8 g (0.112 mole) of pulverized 7-theophylline acetic acid. The mixture is warmed slightly to bring about complete solution, a very small amount of insoluble matter is filtered off, and the residual aqueous solution concentrated under reduced pressure until all the water has been removed.

A white powder is obtained which, after drying, has a melting point of approximately 200° C (the melting point is not well defined) and which, on analysis, gives the following results:

| Calculated for $C_{16} H_{29} O_6 N_7 S$ | Calculated | Found |
|---|---|---|
| C% | 42.93 | 43.2 |
| H% | 6.54 | 6.84 |
| N% | 21.91 | 22.1 |
| S% | 7.16 | 7.31 |

The salt shows a maximum absorption of ultraviolet light at 273 mu with an optical density of 0.49 at a concentration of $0.5 \times 10^{-4}$ in water which has been buffered to pH 5.

2. The double salt of 7-theophylline acetic acid, and N-acetylmethionine with ethylenediamine.

21.2 g (0.11 mole) of acetylmethionine is dissolved in 100 ml of water in the presence of 6.71 g (0.111 mole) of ethylenediamine, and 26.4 g (0.111 mole) of 7-theophylline acetic acid is added while stirring. The mixture is refluxed for a quarter of an hour, filtered to remove impurities and the solution concentrated under reduced pressure.

A slightly colored powder is obtained which, after drying in vacuo, melts at 155° C (melting point not well defined) and still contains approximately 3% by weight of water. On analysis, a sample which has been dried to constant weight under reduced pressure over phosphoric anhydride gives the following results.

| Calculated for $C_{18} H_{31} O_7 N_7 S$ | Calculated | Found |
|---|---|---|
| C% | 44.15 | 44.3 |
| H% | 6.39 | 6.51 |
| N% | 20.03 | 20.36 |
| S% | 6.54 | 7.04 |

The ultraviolet absorption spectrum for this salt shows a maximum at 273 mµ, with an optical density of 0.48 at a concentration of $0.5 \times 10^{-4}$ in water which had been buffered to pH 5.

3. The double salt of 1 mole of 7-theophylline acetic acid and 1 mole of N-acetyl-L-cysteine with 1 mole of ethylenediamine.

6.77 g (0.112 mole) of ethylenediamine and 18.3 g (0.112 mole) of N-acetyl-L-cysteine are dissolved in 100 ml of water and 26.8 g (0.112 mole) of pulverized 7-theophylline acetic acid is added. The mixture is heated to boiling for a few minutes, treated with 2 g of decolorizing black, filtered, and the water removed under reduced pressure.

A powder is obtained which melts at approximately 135° C (melting point not well defined), which has a specific rotation of +7.5° (C = 10 in water), and which gave the following results on analysis:

| Calculated for $C_{16} H_{27} O_7 N_7 S$ | Calculated | Found |
|---|---|---|
| C% | 41.63 | 42.0 |
| H% | 5.91 | 6.05 |
| N% | 21.25 | 21.30 |
| S% | 6.95 | 7.13 |

4. The double salt of 1 mole of 7-theophylline acetic acid and 1 mole of S-carboxymethylcysteine with 1 mole of ethylenediamine.

20.5 g (0.112 mole) of S-carboxymethylcysteine is dissolved in 100 ml of water containing 6.77 g (0.112 mole) of ethylenediamine and, while stirring, 26.8 g (0.112 mole) of pulverized 7-theophylline acetic acid is added. The mixture is heated to reflux, treated with 2 g of decolorizing black, filtered, concentrated under reduced pressure and the powder obtained dried. In this way there is obtained a dihydrate which contains substantially 8.18% by weight of water, which has the general formula $C_{16} H_{27} O_8 N_7 S, 2H_2O$, which melts in the neighborhood of 170° C (ill defined), and which, when analyzed, gives the following results when the calculations have been corrected for the presence of water:

| Calculated for $C_{16} H_{27} O_8 N_7 S$ | Calculated | Found |
|---|---|---|
| C% | 40.23 | 40.1 |
| H% | 5.71 | 5.70 |
| N% | 20.54 | 20.31 |
| S% | 6.71 | 6.85 |

The anhydrous salt has a specific rotation of 12.6° (C = 10 in water).

5. The double salt of 1 mole of 8-chloro-7-theophylline acetic acid and 1 mole of N-acetylthiazolidine-4-carboxylic acid with 1 mole of ethylenediamine.

In a similar manner, 17.5 g (0.1 mole) of N-acetylthiazolidine-4-carboxylic acid is dissolved in 100 ml of water containing 6.0 g (0.1 mole) of ethylenediamine. While stirring vigorously, 27.2 g (0.1 mole) of 8-chloro-7-theophylline acetic acid (melting point 199° C) is added. A solution is obtained which is heated to reflux and treated, while hot, with decolorizing black.

After filtering and concentration to dryness, a white powder is obtained which is completely soluble in water and which has an ill-defined melting point (accompanied by decomposition) but is near to 170° C.

Analysis of the anhydrous product gave the following result:

| Calculated for $C_{17}H_{26}ClN_7O_7S$ | | |
|---|---|---|
| | Calculated | Found |
| C% | 40.23 | 40.37 |
| H% | 5.16 | 5.25 |
| N% | 19.32 | 19.15 |
| Cl | 6.99 | 7.03 |
| S% | 6.31 | 6.27 |

The salts of the present invention, which may be used in the form of aqueous solutions thereof, have the properties of theophylline as well as those of sulphur-containing molecules. They may be used with advantage in the treatment of respiratory complaints, and are of very low toxicity: When administered by the intravenous route to the mouse in a dose of 500 mg/kg, they produce no ill effects.

The activity of the salts of the present invention has been tested by the following methods:
1. Effect on the respiratory system
   a. Examination of bronchodilatory effects by the Konzett method.
   b. Analeptic effect on respiration in an animal whose respiration has been depressed by administration of morphine or barbiturates. Measurements were made of the pressures of oxygen and carbon dioxide in the arterial blood.
   c. Fluidifying effect on bronchial mucous in the rat which has inhaled sulphur dioxide.
2. Effect on the cardiovascular system
   a. Effect on arterial pressure,
   b. Effect on the pulse rate (electro-cardiogram).
3. Diuretic effect.

The results obtained make it possible to demonstrate the effect on the respiratory system. The salts according to the invention exhibit:
   a. A very distinct bronchodilatory effect, although slightly less than the effect of theophylline. In the guinea-pig, they counteract histamine-induced bronchial spasms.
   b. In an aminal whose respiration has been depressed either by administration of morphine or barbiturates, the substances under examination cause an increase in the frequency, and amplitude of respiratory motions. An improvement in the oxygen pressure in the arterial blood is observed.
   c. In the rat exposed to sulphur dioxide, the various products according to the invention, when administered by the oral route, reduce the number of mucopurulent obstructions and have a marked cleansing effect on the bronchi and alveoli. Thus, they exert a distinct lytic effect on retained mucous. Furthermore, in preventing fresh obstruction and healing the associated bronchopulmonary lesions, the substances would appear to exert a direct tropic role upon the epithelial cells, one of the functions of which is to regulate the mucous-secreting function.

Furthermore, the effect on the cardiovascular system is shown by a lowering of the arterial pressure as a function of the dosage, without any alteration in the pulse rate or any significant alteration in the electrocardiogram being noted.

The diuretic effect, which was studied in rats which had drunk an excess of water is not great.

The salts of the present invention may be used either alone or together with other active ingredients in the presence of any compatible excipients and may be used in all the conventional pharmaceutical forms, such as tablets (which may be sugar-coated), ampoules the contents of which are intended to be taken orally, syrups, sprays, and suppositories, for treating bronchial conplaints and complaints of the respiratory system.

What is claimed is:

1. A double salt of ethylenediamine having the general formula:

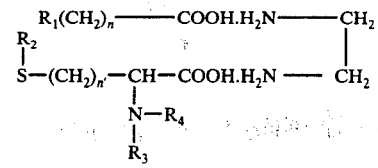

wherein $R_1$ is a theophylyl or a theophylyl group substituted in the 8-position with a chloro or bromo group, $n$ is an integer from 1 to 4 and

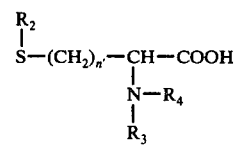

represents an aminocarboxylic acid, wherein $R_2$ represents a hydrogen atom, a methyl group or a $-CH_2$-COOH group; $n'$ is an integer equal to 1 or 2; $R_3$ represents a hydrogen atom or a $-COCH_3$ group; $R_4$ represents a hydrogen atom and when sulphur and nitrogen are in a heteromonocyclic ring, $n'$ is 1, and $R_2$ and $R_4$ represent a methylene group.

2. A double salt according to claim 1 in which $n$ is 1, 2 or 3.

3. A double salt according to claim 8 in which the $R_1(CH_2)_n$—COOH is 7-theophyllineacetic acid.

4. A double salt according to claim 1, wherein acid represented by $R_1(CH_2)_n$—COOH is 8-chloro-7-theophylline acetic acid.

5. A double salt according to claim 1, wherein the acid represented by $R_1(CH_2)_n$—COOH is 7-theophylline propionic acid.

6. A double salt according to claim 1, wherein the acid represented by $R_1(CH_2)_n$—COOH is 8-chloro-7-theophylline propionic acid.

7. A double salt according to claim 1, wherein the acid represented by $R_1(CH_2)_n$—COOH is 7-theophylline butyric acid.

8. A double salt according to claim 1, wherein the acid respresented by $R_1(CH_2)_n$—COOH is 8-chloro-7-theophylline butyric acid.

9. A double salt according to claim 1 in which the acid represented by the formula:

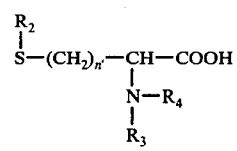

is cysteine, methionine, N-acetylmethionine, N-acetylcysteine or S-carboxymethylcysteine.

10. A double salt according to claim 1 in which the acid represented by the formula:

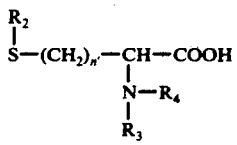

is N-acetylthiazolidine-4-carboxylic acid.

11. The double salt of 1 mole of 7-theophylline acetic acid and 1 mole of methionine with 1 mole of ethylenediamine.

12. The double salt of 1 mole of 7-theophylline acetic acid and 1 mole of N-acetylmethionine with 1 mole of ethylenediamine.

13. The double salt of 1 mole of 7-theophylline acetic acid and 1 mole of N-acetyl-L-cysteine with 1 mole of ethylenediamine.

14. The double salt of 1 mole of 7-theophylline acetic acid and 1 mole of S-carboxymethylcysteine with 1 mole of ethylenediamine.

15. The double salt of 1 mole of 8-chloro-7-theophylline acetic acid and 1 mole of N-acetylthiazolidine-4-carboxylic acid with 1 mole of ethylenediamine.

* * * * *